United States Patent [19]
Newman et al.

[11] Patent Number: 5,082,540
[45] Date of Patent: Jan. 21, 1992

[54] FLUORIDE ION SENSITIVE MATERIALS

[75] Inventors: Jeffrey D. Newman, Hail Weston, Great Britain; Ramin Pirzad, Bristol, United Kingdom; David C. Cowell, Wotton-Under-Edge, United Kingdom; Antony A. Dowman, Nailsea, United Kingdom

[73] Assignee: The Secretary of State for Defence in Her Britannic Majesty's Government of the United Kingdom of Great Britain and Northern Ireland, London, England

[21] Appl. No.: 610,240

[22] Filed: May 7, 1990

[51] Int. Cl.$^5$ .............................................. B22F 3/16
[52] U.S. Cl. .............................. 204/153.13; 419/31; 419/48
[58] Field of Search ................ 419/48, 31; 204/153.13

[56] References Cited
U.S. PATENT DOCUMENTS 3,431,182  3/1969  Frant .................... 204/153.13
4,500,406  2/1985  Weyand et al. ............... 419/48
4,591,482  5/1986  Nyce ........................ 419/48
4,676,949  6/1987  Miyashita et al. ........... 419/31
4,761,262  8/1988  Ogata et al. ................ 419/48

FOREIGN PATENT DOCUMENTS 173237  12/1920  United Kingdom ............. 419/31

OTHER PUBLICATIONS

Frederick A. Lowenheim, Electroplating, 1978, pp. 93-98.

Primary Examiner—John Niebling
Assistant Examiner—Bruce Bell
Attorney, Agent, or Firm—Nixon & Vanderhye

[57] ABSTRACT

A fluoride ion sensitive material suitable for use as the active component in a fluoride ion sensitive electrode comprises a sintered mixture comprising of up to 99.9 molar % of Lanthanum trifluoride and from 0.1 to 20 molar % Calcium difluoride formed from a body that has been pressed at $10^7$ Pa or more and then sintered in a inert atmosphere at 900° C. or more.

16 Claims, 2 Drawing Sheets

FLUORIDE ION SENSITIVE MATERIALS

BACKGROUND OF THE INVENTION

The present invention pertains to fluoride ion sensitive material suitable for use in the manufacture of active components for fluoride ion-sensitive electrodes for electro-analytic monitoring purposes. The present invention further provides a method for manufacturing said material of the invention which allows the use of polycrystalline starting materials and does not require highly reactive atmospheres used by some of the known methods of making fluoride ion sensitive materials.

The conventional fluoride ion-sensitive electrode (FISE) developed by Frant and Ross in 1966 utilizes a single crystal of $LaF_3$ doped with $EuF_2$ as its sensing element. The crystal has low solubility and low resistance, both of which are desirable for a low detection limit and a fast response. That electrode exhibits Nernstian behaviour from saturated to $10^{-5}$ M solutions of $F^-$, and a detection limit of below $10^{-6}$ M $F^-$. The only significant interferent is the $OH^-$ ion and this can be avoided by operating the system in acid solution.

The FISE is second only to the glass pH electrode, in terms of its selectivity, and few other ion sensitive electrodes can match its speed of response, range of operation and stability; all features making it very suitable for use as the sensing element in a biosensor. Particular applications include detection of organofluoride compounds by use in conjunction with such release agents as peroxidases. In this technique peroxidase is use to cause fluoride ion release from said organofluoride which may then be measured as related to said fluoride level. Thus the FISE may be coupled to any reaction scheme that releases $F^-$ ions which can be detected rapidly with no significant interference.

As a disposable biosensor the FISE is limited by the high cost of the single crystal device and thus an alternative more easily produced low cost device would be advantageously provided with such use in mind. However the excellent properties of the current FISE have resulted in few reports of alternative methods of production.

MacDonald and Toth, Anal. Chem. Acta. 1968, 41, 99, abandoned their work on electrodes produced from polycrystalline, low-solubility fluoride compounds supported in an inert matrix of materials such as polyvinylchloride or silicone rubber soon after the Frant and Ross electrode was described due to the latter devices superiority.

The patent relating to the single crystal material, U.S. Pat. No. 3,431,182, showed that several methods for the manufacture of FISEs had been investigated using insoluble monocrystalline and polycrystalline fluoride salts; monocrystalline $LaF_3$, $PrF_3$, $CeF_3$, $NdF_3$ and polycrystalline $PbF_2$ and $BiF_3$ were tested. The monocrystalline devices were shown to have the same disadvantage of expense as the conventional device, while the polycrystalline electrodes exhibited poor responses and were more susceptible to interference.

Improved performance electrodes have been made from polycrystalline starting materials by Hirata et al, as reported in Chem. Lett., 1974, 1451, whereby a mixture of $LaF_3$, $CaF_2$, and $EuF_3$ was heated under pressure in an atmosphere of hydrogen fluoride gas to a temperature of 1200° C. These workers reported that their material had slightly improved electrode characteristics compared with the single crystal device but the process used to produce it was complex.

To date possibly the least expensive method for providing fluoride sensitive electrode material having satisfactory properties is that provided by East German Patent DD 227,800 wherein a silicon disc was vacuum coated with $LaF_3$ and bonding a wire to the rear of the disc using silver-loaded epoxy resin. The disc was then sealed into a conventional electrode body using epoxy resin. As can be seen, no satisfactory electrode material forming process yet exists which is capable of providing satisfactory electrodes from polycrystalline starting materials which does not use hazardous atmospheres or complex methods.

SUMMARY OF THE INVENTION

It is an object of the present invention to provide a fluoride ion sensitive material suitable for use as the active material in fluoride ion sensitive electrodes.

It is another object of the present invention to provide a fluoride ion sensitive material suitable for use as the active material in fluoride ion sensitive electrodes having a Nerstian response over the range $10^{-2}$ to $10^{-5}$ M $F^-$.

It is a still further object of the present invention to provide a fluoride ion sensitive material suitable for use as the active material in fluoride ion sensitive electrodes having detection limits below $10^{-6}$ M $F^-$.

It is a still further object of the present invention to provide a fluoride ion sensitive material suitable for use as the active material in fluoride ion sensitive electrodes having a response time of less than one minute.

It is a still further object of the present invention to provide a method of providing a fluoride ion sensitive material such that it is feasible to manufacture disposable electrodes from it.

It is still further object of the present invention to provide such a process whereby cost is reduced such that production of 'disposable' FISEs might be facilitated whilst maintaining sensitivity and response characteristics.

These and other objects of the present invention are attained by a method of producing a fluoride ion sensitive material comprising the steps of (a) producing a mixture comprising up to 99.9 molar % Lanthanum fluoride and between 0.1 to 20 molar % of Calcium fluoride, (b) mechanically forming said mixture under pressure in excess of $10^7$ Pa and (c) sintering the resultant formed body at a temperature in excess of 900° C. in an inert atmosphere.

The present invention is based upon a method of mechanically forming a pressed body which may be sintered without use of a vigorous atmosphere, such as hydrogen fluoride, whilst not requiring inclusion of significant amounts of Europium fluoride in the material to be sintered or use of single crystal material to achieve the desired fluoride ion sensitivity.

Preferably the mechanical forming is carried out at above $10^8$ Pa, more preferably at $10^9$ Pa or above, and the sintering is carried out at between 1000° and 1400° C., more preferably 1200° C. Sintering may be typically carried out for a time over 30 minutes, more typically over 1 hour but preferably for 2 hours or more.

The mixture from which the body is pressed comprises essentially of a major portion, up to 99.9 molar %, of Lanthanum fluoride and from between 0.1 and 20 molar % of Calcium fluoride. Further metal fluorides may of course be present in the said mixture within the limits outlined, e.g.: Europium fluoride may be included, but no advantage is envisaged by doing so in the light of the intended use and the satisfactory nature of the material produced without said additional fluorides.

The mixture preferably comprises from between 90 and 99.9 molar % of Lanthanum fluoride and from between 0.1 and 10 molar % Calcium fluoride. More preferably the mixture comprises from between 92 and 98 molar % Lanthanum fluoride and from between 2 and 8 molar % Calcium fluoride. Most preferably the mixture comprises about 96 molar % Lanthanum fluoride and about 4 molar % Calcium fluoride.

The body is mechanically formed by exerting a pressure of $10^7$ Pa or more upon the mixture, preferably of $10^8$ Pa or more and most preferably $10^9$ Pa. The mixture for pressing is produced by grinding the crystalline metal fluorides into a powder form, preferably by use of conventional industrial grinding apparatus but may be satisfactorily provided by use of a simple glass mortar and pestle.

Sintering of the pressed body is carried out in an inert atmosphere, typically comprising a gas such as nitrogen which does not react with the mixture components at the sintering temperature.

Although 100% Lanthanum fluorides may be produced having a slightly sub-Nernstian response, the present inventors have found that the inclusion of Calcium fluoride into the body reduces the resistance of the sintered product; addition of between 1 and 8 molar % of Calcium fluoride providing a decrease in resistance to about one third and, most advantageously, addition of about 4 molar % of Calcium fluoride provides a decrease in resistance to about one fifteenth.

Furthermore, the inclusion of these levels of Calcium fluoride results in a material having a more Nernstian response over the range $10^{-2}$ to $10^{-5}$ M F$^-$ in addition to lowering the detection limit. Again, about 4 molar % of Calcium fluoride provides the best detection limit as increasing the levels above this results in non optimal detection limits, less reproducibility and slower response times.

By comparison, substitution of the Calcium fluoride by Europium fluoride and sintering under the conditions used in the present method results in poor responses and high resistances. Control experiments using 100 molar % Calcium Fluoride or Europium fluoride powders provides sintered bodies having very high resistances and giving no response with up to $10^{-2}$ M F$^-$.

It is known that Calcium fluoride forms a eutectic mixture with Lanthanum fluoride, at about 8 molar % of CaF$_2$, which lowers the melting point of the material to 1300° from 1493° C. This results in a far higher degree of diffusion within the ionic lattice at 1200° C. thus allowing increased infiltration of divalent ions into the Lanthanum fluoride and resulting in a more densely packed structure, both causing a sharp drop in resistance.

It is desirable that electrodes produced using the materials of the present invention should be kept in dry conditions, e.g.: in a container including a dessicant material, up until the time of use as it has been noted that resistance falls but response worsens when new electrode material has been left undessicated for periods of 2 weeks before testing. This feature is clearly illustrated in FIG. 3.

DETAILED DESCRIPTION OF THE INVENTION

Figure 1:
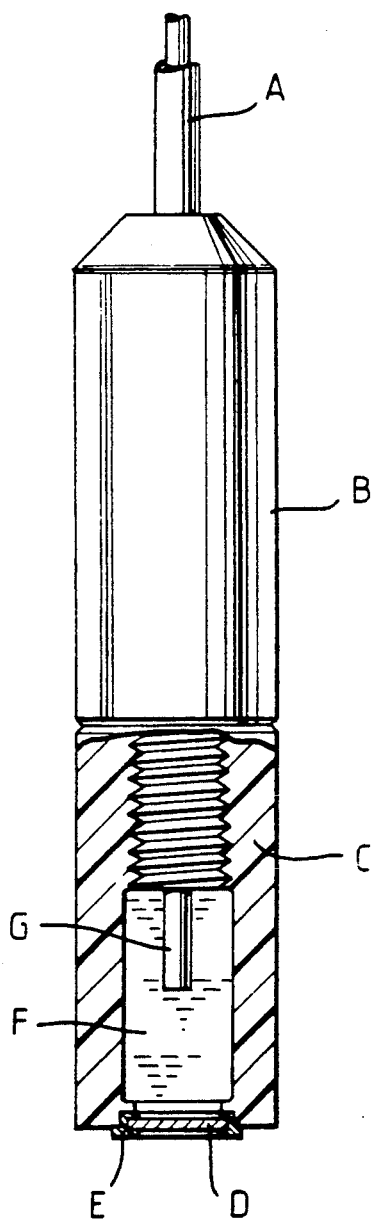
FIG. 1. a schematic diagram of an electrode employing the material of the present invention as active fluoride ion sensitive material.

With reference to the figures, materials made in accordance with the present invention were incorporated as discs D into the electrode of the type shown in FIG. 1. In said electrode of FIG. 1, A designates a coaxial cable, B an electrode body, C a disposable tip, E an epoxy resin seal, F an inner filling solution and G an Ag-AgCl wire.

A 15 tonne hydraulic press and 5 mm pellet die were acquired from Specac (Orpington, Kent, UK) and a Model 361 furnace containing an Al$_2$O$_3$ inner tube was obtained from Stanton Ryecroft (London, UK). CY130-/HY1300 epoxy resin from Ciba-Geigy (Duxford, Cambridgeshire, UK) was used. A Model CRL calomel reference electrode from Russel pH (Auchtermachty, Fife, UK) was used for comparison. Johnson Matthey (Royston, Cambridgeshire, UK) supplied 99.99% pure LaF$_3$, CaF$_2$ and EuF$_3$ while all other reagents were of AnalaR grade and provided by BDH (Poole, Dorsetshire, UK). Acetate buffer (pH 5.5) was prepared from 17.2 ml of glacial acetic acid, 2.013 g of NaCl and 10.2 g of NaOH made up to 1 liter with distilled water. Stock solutions of F$^-$ were made up in this buffer using NaF while electrode inner filling solution was made up with 0.1 M NaF and 0.1 M KCl saturated with AgCl. EuF$_2$ was synthesised by the technique of Koksbang and Rasmussen, Acta. Chem. Scand., 1985, A39, 761 whereby EuF$_3$ was reduced with silicon powder at a temperature of 900° C. for 2 hours in a stream of dry nitrogen. The silicon is converted to gaseous SiF$_4$ which is removed by the nitrogen stream to leave EuF$_2$ powder behind which was stored over silica gel in a desiccator prior to use to avoid oxidation in accordance with the equation:

$$4EuF_3 + Si \rightarrow 4EuF_2 + SiF_4$$

Oxygen free nitrogen was provided by BOC (Guildford, Surrey, UK).

Electrodes were formed from 0.1 g of polycrystalline LaF$_3$, CaF$_2$, EuF$_2$ or mixtures of these, ground into a fine powder using a glass mortar and pestle and then pressed at a pressure of $1 \times 10^9$ Pa to form discs about 1 mm thick. The discs were placed on a platinum boat in batches of five and heated in a stream of dry nitrogen, typically for 2 hours at 1200° C., but higher temperatures were also used. A cooling rate was used limited to 10° C. min$^{-1}$ to avoid thermal shock damage to the discs.

Epoxy resin was used to attach the discs to unplasticized polyvinylchloride electrode tips and the bonded assembly was allowed at least 24 hours at room temperature to set. The electrode design allows the tip to be discarded after use with the remainder of the electrode being reusable. Electrodes were stored in a dessicator at room temperature over silica gel.

The electrodes were immersed in $10^8$ M F$^-$ in acetate buffer, and successive additions of small volumes of F$^-$ standard solutions were made after the electrode potential had stabilized in each case. Decades of concentration up to $10^{-2}$ were covered. Equilibrium values of potentials were found using the antilogarithm of the potential versus reciprocal time plot whereby extrapolation to the potential at time infinity gives the equilibrium value. Interference tests by the fixed-interferent method of IUPAC, Pure Appl. Chem., 1976, 48, 127. whereby Cl$^-$, OH$^-$ and HPO$_4^{2-}$ were tested for interference at a fixed concentration of $10^{-2}$ M. All experiments were carried out between 18° and 22° C. without temperature control.

The resistance $R_1$ of the electrode was measured with the electrode, and reference connected to a high input impedance amplifier, immersed in $10^{-2}$ M F$^-$ solution. First the potential difference ($V_1$) is read and then the meter is shunted with a suitable high resistor $R_2$ and the new potential difference ($V_2$) then read. The resistance of the electrode is calculated using the relationship:

$$R_1 = R_2(V_1/V_2 - 1).$$

Figure 2:
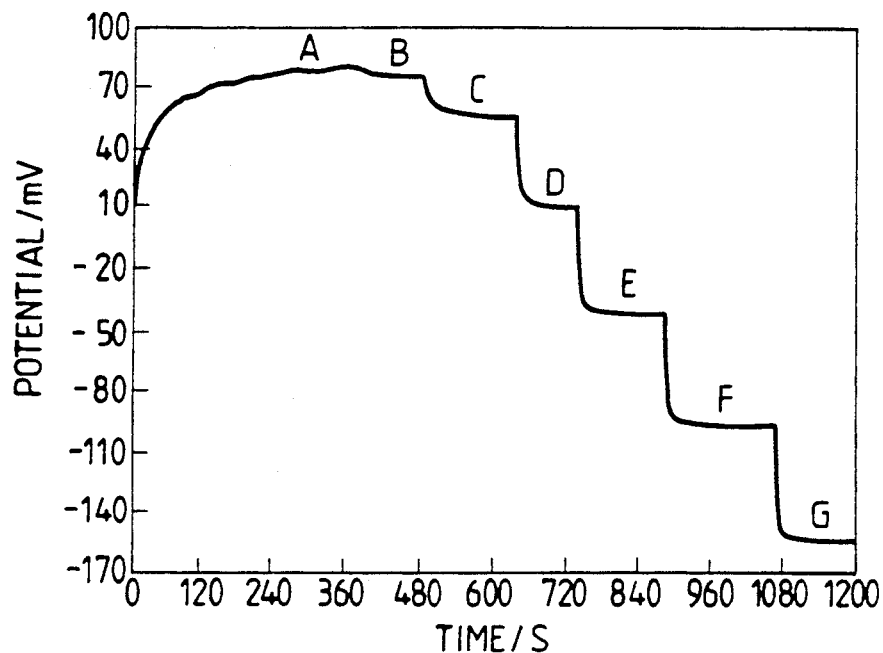
FIG. 2. a graph showing the relationship between the potential set up by an electrode employing the material of the present invention as active fluoride ion sensitive material with time as the concentration of F$^-$.

Mean values of the slopes obtained between $10^{-2}$ and $10^{-5}$ M F$^-$ and the electrode resistances and detection limits for various compositioned materials are shown in Table 1 below. A typical response for one of the 4 molar % CaF$_2$ - 96 molar % LaF$_3$ electrodes is shown in FIG. 2 where the concentration changes in decade steps from $10^{-8}$ M to $10^{-2}$ M F$^-$. A larger batch of these electrodes was used to calculate selectivity coefficient values for Cl$^-$, OH$^-$ and HPO$_4^{-2}$ ion interference which were determined as follows:

$$Log \, k^{pot}_{F,Cl} = -3.69$$

$$Log \, k^{pot}_{F,OH} = -1.82$$

$$Log \, k^{pot}_{F,HPO4} = -2.24$$

air results in electrodes of reduced sensitivity at low fluoride ion levels, and reuse of electrodes that have been immersed in aqueous solutions will generally have a similar result. Storage of the electrodes of the present invention in a dessicator for 2 months resulted in no significant loss of responsivity.

Figure 3:
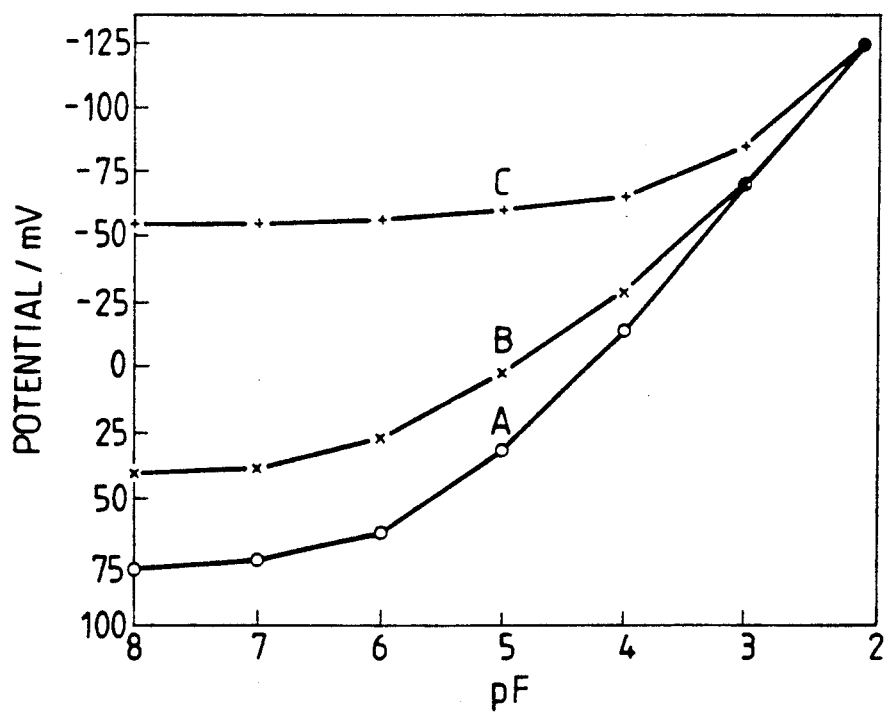
FIG. 3. a graph showing the effect of storage conditions on the response curves of electrodes employing the material of the present invention as active fluoride ion sensitive material.

FIG. 3 shows: A, a typical response curve of a sintered Lanthanum trifluoride electrode that had been stored in a dessicator; B, an electrode stored in air for 2 weeks; and C, an electrode that had been used previously.

The mean response times of five electrodes for a decade change in the concentration of fluoride ion, calculated over four ranges, were compared with those obtained from three separate Russell electrodes and the results obtained are shown in Table 2. The antilogarithm of the potential versus reciprocal time plots, described earlier for finding the equilibrium value, was used to calculate the time taken for the electrode to reach within 1 mV of the equilibrium value, as recommended by IUPAC.

TABLE 2

| Concentration/M | | Response time/s | | | |
|---|---|---|---|---|---|
| | | Polycrystalline | | Commercial | |
| Initial | Final | Mean | SD | Mean | SD |
| $10^{-6}$ | $10^{-5}$ | 111 | 39 | 110 | 60 |
| $10^{-5}$ | $10^{-4}$ | 41 | 16 | 20 | 11 |
| $10^{-4}$ | $10^{-3}$ | 33 | 10 | 9 | 3 |
| $10^{-3}$ | $10^{-2}$ | 46 | 15 | 4 | 1 |

It should be realised that discs with polished surfaces will be more sensitive to F$^-$ concentration than those with unpolished surfaces. Use of commercially available abrasive paper is effective enough to improve sensitivity in this regard.

What is claimed is:

1. A process for preparation of a sintered material suitable for use as the fluoride ion sensitive component in a fluoride ion sensitive electrode exhibiting a Nernstian response to fluoride ion concentrations of $10^{-2}$ to $10^{-8}$ molar, said process comprising:

(1) mechanically forming a mixture consisting essentially of from 80 to 99.9 molar % crystalline lanthanum trifluoride and from 0.1 to 20 molar % crystal-

TABLE 1

| DISC COMPOSITION MOLAR % | | | 1 | 2 | 3 | 4 | 5 | 6 | 7 |
|---|---|---|---|---|---|---|---|---|---|
| LaF$_3$ | CaF$_2$ | EuF$_2$ | hr | mv | decade$^{-1}$ | MOhm | $10^{-6}$ | M | No |
| 100 | 0 | 0 | 2 | −49.5 | 6.7 | 1100 | 9.0 | 13 | 10 |
| 99 | 1 | 0 | 2 | −55.3 | 2.3 | 2.1 | 2.8 | 2.0 | 5 |
| 98 | 2 | 0 | 2 | −54.3 | 1.0 | 1.1 | 2.6 | 1.3 | 5 |
| 96 | 4 | 0 | 2 | −55.2 | 0.6 | 3.8 | 0.60 | 0.2 | 5 |
| 96 | 4 | 0 | 6 | −56.2 | 0.8 | 3.1 | 1.6 | 0.51 | 3 |
| 94 | 6 | 0 | 2 | −50.4 | 2.6 | 2.5 | 24 | 11 | 5 |
| 92 | 8 | 0 | 2 | −57.4 | 3.1 | 2.5 | 3.6 | 2.2 | 5 |
| 0 | 100 | 0 | 2 | * | * | : | * | * | 5 |
| 99 | 0 | 1 | 2 | −16.7 | 4.5 | 1200 | 470 | 70 | 5 |
| 98 | 0 | 2 | 2 | −38.0 | 7.1 | 1300 | 68 | 48 | 5 |
| 96 | 0 | 4 | 2 | −38.3 | 12.8 | 740 | 120 | 140 | 5 |
| 94 | 0 | 6 | 2 | −33.6 | 13.8 | 760 | 160 | 220 | 4 |
| 92 | 0 | 8 | 2 | −26.8 | 17.7 | 3100 | 290 | 220 | 4 |
| 0 | 0 | 100 (EuF$_3$) | 2 | * | * | : | * | * | 5 |
| Commercial electrode | | | | −57.4 | 0.8 | 1.2 | 0.91 | 0.63 | 3 |

* = No reading possible
: = resistance too high to measure
1 = Sintering time, 2 = Mean slope, 3 = Standard deviation 4 = Mean resistance. 5 = Mean detection limit, 6 = Standard deviation 7 = Number tested Storage of the electrode tips of the present invention in a dry atmosphere is found to improve the Nernstian nature of the response to fluoride ions, particularly at low concentrations of the ion. Thus exposure to moist line calcium difluoride under a pressure of $10^7$ Pa or more, and then (2) sintering it at a temperature of 1,000° C. or above in an inert atmosphere.

2. A process according to claim 1 wherein the sintering temperature is from 1,000° C. to 1,400° C.

3. A process according to claim 2 wherein the sintering temperature is about 1,200° C.

4. A process according to claim 1 wherein the lanthanum trifluoride and calcium difluoride comprise crystalline materials ground into a powder form.

5. A process according to claim 1 wherein the lanthanum trifluoride and calcium difluoride comprise polycrystalline materials ground into powder form.

6. A process according to claim 1 wherein the mixture consists essentially of from 92 to 98 molar % Lanthanum trifluoride and from 2 to 8 molar % calcium difluoride.

7. A process according to claim 6 wherein the mixture comprises about 96 molar % lanthanum trifluoride and about 4 molar % calcium difluoride.

8. A process according to claim 6 wherein said mixture also includes less than 0.1 molar % europium difluoride or europium trifluoride.

9. A process according to claim 1 wherein the mixture is mechanically formed by pressing at $10^8$ Pa or more.

10. A process according to claim 9 wherein the mixture is mechanically formed by pressing at $10^9$ Pa or more.

11. A process according to claim 1 wherein the sintering is carried out for 30 minutes or more.

12. A process according to claim 11 wherein the sintering is carried out for 1 hour or more.

13. A process according to claim 12 wherein the sintering is carried out for 2 hours or more.

14. A process according to claim 1 or 11 wherein the sintering is carried out under a nitrogen gas atmosphere.

15. A process according to claim 1 or 11 wherein the sintering is carried out under a dry nitrogen gas atmosphere.

16. A process according to claim 1 including the additional step of (3) polishing the surface of the sintered material.

* * * * *